United States Patent [19]

Hursey et al.

[11] Patent Number: 4,822,349

[45] Date of Patent: Apr. 18, 1989

[54] METHOD OF TREATING WOUNDS

[76] Inventors: Francis X. Hursey, 27 Keeney Ave., W. Hartford, Conn. 06107; Fernand J. Dechene, 2931, New Britain, Conn. 06051

[21] Appl. No.: 603,884

[22] Filed: Apr. 25, 1984

[51] Int. Cl.⁴ .............................................. A61L 15/00
[52] U.S. Cl. ..................................... 604/367; 128/156
[58] Field of Search ....................... 604/367; 128/156; 424/27, 28, 14, 157, 445, 446, 447

[56] References Cited

U.S. PATENT DOCUMENTS 4,525,410  6/1985  Hagiwara et al. .................. 604/367

Primary Examiner—C. Fred Rosenbaum
Assistant Examiner—Mark F. Colosimo
Attorney, Agent, or Firm—McCormick, Paulding & Huber

[57] ABSTRACT

A molecular sieve material, preferably zeolite, is provided in a suitable binder and in sterilized form such that it can be applied directly to an open wound. The wound or opening to be treated is completely covered in order to achieve the best results.

3 Claims, No Drawings

METHOD OF TREATING WOUNDS

SUMMARY OF THE INVENTION

This invention relates generally to a novel method for treating bleeding in warm blooded mammals, and deals more particularly with the use of a molecular sieve material for this purpose.

In carrying out the method of the present invention a molecular sieve material, preferably zeolite, is provided in a suitable binder and in sterilized form such that it can be applied directly to an open wound. The wound or opening to be treated is completely covered in order to achieve the best results. The blood from the wound is absorbed in the interstices present in the preferred dehydrated sieve material, zeolite, with the result that increased coagulation is achieved due to the fact that the blood is demoisturized as a result of passing through the layer of zeolite applied to the wound. A further advantage is achieved as a result of the heat generated in the exothermic action of the zeolite material on the moist blood, and this heat cauterizes the wound. This added advantage coupled with the moisture absorbing characteristics of zeolite provides a very efficient base for any ointment or salve such as are sold for use in bandaging materials.

DETAILED DESCRIPTION

Zeolite crystals are available indigenously in New Jersey, Long Island and along the Bay of Fundy in Nova Scotia. Many varities of these naturally occuring minerals have been found. Zeolite minerals have also been found in sedimentary environments and may have been produced by the alteration of volcanic ash by gradually receding lake waters. The desert areas of the western United States are a good example of this occurence.

Zeolite has also been produced synthetically by duplicating this natural hydrothermal process as a result of which zeolite minerals are assumed to have been formed in nature. About thirty species of zeolite have been prepared in a pure state as a result of carefully controlled various parameters, such as the initial composition of the gel, crystallization temperature, and type of reactant. Polymerization of aluminate and silicate anions produces zeolite and depending upon the type of reactant used and the crystalization temperature achieved some of these synthetic species appear to be structurally related to natural zeolites. Others have no known analog from among such natural zeolites. Generally speaking more open zeolite molecular structures are crystalized from sodium containing gels rather than from those which contain potassium, as for example the alkyd ion. The hydrated sodium ion is slightly larger than the hydrated potassium ion. Crystalization of the hydro vs gel exhibits an induction period which can be determined by following the formation of crystals as a function of time, a process apparent as a result of utilizing X-ray techniques. The induction period apparently corresponds to the growth of crystal nuclie to a critical size, followed by the rapid growth of the crystalite to the final zeolite crystals.

Given suitable crystaline and zeolite, one must then dehydrate the zeolite to eliminate water molecules from the cavities within the cystaline structure. This is generally done by the application of heat in a vaccum. The basic framework of the zeolite structure does not appreciably change as a result of the dehydration even under very stringent conditions, and the zeolite can conveniently be sterilized at this point when practicing the method of the present invention.

The crystaline solid remaining after dehydration and sterlization can be highly absorbent for selected gases and vapors. Molecular sized voids permeate the crystals forming the internal surface area or absorption space. The zeolites generally produced for such absorption purposes contain approximately 50 percent by volume of void space for absorbing selected materials. While it is known to utilize zeolite for the absorbtion of water, the present invention deals with use of zeolite for absorbing blood. Due to the interaction between the dipole of the water molecule in the blood with the charge on the zeolite structure the zeolite cavities are essentially filled with moisture from the blood, a result enhanced if a clay binder is used and the zeolite material provided in the form of beads as is sometimes done when adsorption of gases is to be accomplished as for example in the manufacture of humanly breathable oxygen.

Although zeolite molecular sieve materials have been used for absorbing water, and numerous gases, they have never to the knowledge of Applicants here been utilized for the treatment of open wounds or internal and/or external bleeding. Some use has been made of zeolite materials for absorbing hydrocarbons (as for example gasoline and ethylene). But to the knowledge of your Applicants here the use of zeolite material in the treatment of open wounds has not been recognized. A distinct advantage to the use of zeolite for this purpose can be layed to the heat generated as a result of the exothermic action when the zeolite material absorbs moisture from the blood. The heat generated is not excessive, but is sufficient to achieve cauterizing of the wound in addition to the improved coagulation effect had on the blood itself by absorption of the water in the blood.

The various means for utilizing the dehydrated zeolite material referred to herein can be summarized as follows. First of all, the material can be provided in a paste form on a bandage or the like. Alternatively, the material can be dispensed from a small container so as to be readily applied to a bandage or Band-Aid prior to applying the bandage or Band-Aid to the wound. In a small consumer type product a pencil of zeolite material in a binder with or without an aluminum sulfate filler to achieve selective application to small cuts or blemishes that have been caused or aggravated by shaving or the like. Finally, the zeolite material might also be provided in a form more suitable for surgical emergencies and military paramedic situations.

We claim:

1. A method in the medical treatment of warm blooded mammals for reducing the flow of blood from an external wound or other opening in the heart, vein, artery or other internal organ,
    (a) providing dehydrated zeolite molecular sieve material in a sterilized form suitable for use in or on a person to be treated,
    (b) applying said zeolite molecular sieve material directly to the wound or other opening from which blood is emanating so as to completely cover the wound or opening in order that zeolite molecular sieve material absorb water from the blood to achieve a coagulation effect, and heat the tissue adjacent the wound where the moist blood comes into contact with the zeolite molecular sieve material to cauterize such tissue as a result of exothermic action from the zeolite molecular sieve material.

2. The method of claim 1 wherein the zeolite molecular sieve material is provided in a clay-binder and wherein the binder and entrained zeolite molecular sieve material are provided in the form of beads.

3. The method of claim 1 wherein the zeolite molecular sieve material is provided on a bandage so that the application step is a two step process fulfilled by applying said material directly to the wound only after it has been first applied to the bandage.

* * * * *